United States Patent
Gontarz et al.

(10) Patent No.: US 7,806,934 B2
(45) Date of Patent: Oct. 5, 2010

(54) RADIALLY COMPRESSED DEHYDRATED SPINAL NUCLEUS IMPLANTS

(75) Inventors: Gerald Gontarz, Spotswood, NJ (US); Ann Prewett, Bloomfield Hills, MI (US)

(73) Assignee: Replication Medical Inc., Cranbury, NJ (US)

( * ) Notice: Subject to any disclaimer, the term of this patent is extended or adjusted under 35 U.S.C. 154(b) by 0 days.

(21) Appl. No.: 11/303,767

(22) Filed: Dec. 16, 2005

(65) Prior Publication Data

US 2006/0136065 A1 Jun. 22, 2006

(51) Int. Cl.
*A61F 2/44* (2006.01)
(52) U.S. Cl. .................................. 623/17.11
(58) Field of Classification Search ............... 623/17.11, 623/17.12, 17.16; 606/61
See application file for complete search history.

(56) References Cited

U.S. PATENT DOCUMENTS

| | | | |
|---|---|---|---|
| 5,047,055 A | 9/1991 | Bao et al. | |
| 5,458,643 A * | 10/1995 | Oka et al. | 623/17.16 |
| 5,534,028 A | 7/1996 | Bao et al. | |
| 5,562,736 A | 10/1996 | Ray et al. | |
| 5,674,295 A | 10/1997 | Ray et al. | |
| 5,716,416 A * | 2/1998 | Lin | 623/17.16 |
| 5,800,549 A | 9/1998 | Bao et al. | |
| 6,022,376 A | 2/2000 | Assell et al. | |
| 6,132,465 A * | 10/2000 | Ray et al. | 623/17.16 |
| 6,264,695 B1 | 7/2001 | Stoy | |
| 6,533,817 B1 | 3/2003 | Norton et al. | |
| 6,602,291 B1 | 8/2003 | Ray et al. | |
| 6,620,196 B1 * | 9/2003 | Trieu | 623/17.16 |
| 6,764,514 B1 * | 7/2004 | Li et al. | 623/17.12 |
| 2002/0173851 A1 * | 11/2002 | McKay | 623/17.11 |
| 2002/0183848 A1 | 12/2002 | Ray et al. | |
| 2003/0195630 A1 | 10/2003 | Ferree | |
| 2003/0215519 A1 * | 11/2003 | Schwarz et al. | 424/497 |
| 2004/0054413 A1 | 3/2004 | Higham et al. | |
| 2004/0220672 A1 * | 11/2004 | Shadduck | 623/17.16 |
| 2005/0043796 A1 * | 2/2005 | Grant et al. | 623/17.11 |
| 2005/0043801 A1 | 2/2005 | Trieu et al. | |

FOREIGN PATENT DOCUMENTS

| | | |
|---|---|---|
| GB | 2 395 130 A | 5/2004 |
| WO | WO 00/64385 | 11/2000 |

* cited by examiner

*Primary Examiner*—Thomas C Barrett
*Assistant Examiner*—Nicholas Woodall
(74) *Attorney, Agent, or Firm*—Carter, DeLuca, Farrell & Schmidt, LLP (57) ABSTRACT

A radially compressed xerogel spinal nucleus implant is manufactured and utilized for implantation into an intervertebral disc space. The implant has an optimized cross-sectional ellipsoid configuration which facilitates insertion of the implant through a minimal incision in the annulus. Radial compression is achieved by exerting substantially equilateral circumferential compression on an object contained within a radially collapsible member for exerting substantially equilateral circumferential compression on the object. Radial compression may also be achieved by exerting substantially equilateral circumferential compression force on a spinal nucleus implant via gas pressure in a sealed chamber.

55 Claims, 5 Drawing Sheets

RADIALLY COMPRESSED DEHYDRATED SPINAL NUCLEUS IMPLANTS

BACKGROUND

Spinal nucleus implants are known. For example, U.S. Pat. Nos. 5,562,736 and 5,674,295 disclose an implant having a constraining jacket surrounding a hydrogel core. As described therein, a hydrogel material is dehydrated, resulting in an undersized substantially cylindrical gel capsule which is then inserted into the constraining jacket which is then closed to prevent the hydrogel from escaping the confines of the jacket. The implant is rehydrated and conditioned by a series of compressive loads which renders the nucleus body to a partially flattened or oval shape. The implant is then inserted into a retaining tube to maintain the oval shape up until implantation. Alternative embodiments include an outer skin formed by ion implantation which causes outer layer polymerization and functions as the constraining jacket. U.S. Pat. No. 6,022,376 describes an implant made from an amorphous hydrogel polymer core surrounded by a constraining jacket. In one embodiment, the amorphous polymer is poured into one end of the constraining jacket in an unhydrated state, and the jacket then closed. The implant is then massaged to flatten and narrow the implant in preparation for implantation. Alternatively, the amorphous polymer may be injected into the constraining jacket. In one embodiment, an empty constraining jacket is implanted into the disc space and the amorphous polymer is then injected into the constraining jacket. In one embodiment, the amorphous polymer is shaped into a plurality of "microchips" which have been manufactured to have a certain shape. U.S. Pat. No. 6,132,465 is directed to a nucleus implant having a hydrogel core in a constraining jacket. The hydrogel core is inserted into the constraining jacket in a wedge-shaped dehydrated state and then implanted into the nucleus cavity. A final dehydration step is described where the hydrogel core can be forced into certain shapes, i.e., it can be "entirely flat". U.S. Pat. No. 6,602,291 describes a prosthetic spinal disc nucleus which is made with a hydrogel core having a first shape in the hydrated state. It is then placed in a constraining jacket and reshaped to have a second shape in the dehydrated state. The core is configured to transition from the second shape to the first shape on hydration. The second shape may include an elongated shape defined by a leading end, the hydrogel core tapering from the central portion to the leading end, to facilitate insertion through an opening in the annulus. An inherent shape memory attribute is said to be obtained by pouring a hydrogel material, suspended in a solvent into a mold having a shape corresponding to the desired hydrated shape. After a solvent exchange process, the hydrogel core is dehydrated in an oven and inserted into a constraining jacket. The implant is then rehydrated and subjected to conditioning steps by exposure to at least three compressive loads. The implant is then reshaped and dehydrated, i.e., it is placed into a mold having a streamlined shape and then placed in an oven to expedite dehydration of the hydrogel core, which causes the implant to have a streamlined shape. The implant may be compressed while dehydrating, The implant is then maintained in the dehydrated shape prior to implantation. U.S. Pat. No. 6,533,817 is directed to a packaged, partially hydrated prosthetic disc nucleus which includes a prosthetic disc nucleus and a retainer. Upon contact with a hydration liquid, the retainer is said to be configured to allow the hydrogel core to hydrate from the dehydrated state but prevents the core from hydrating to the final hydrated state, i.e., the prosthetic disc nucleus is constrained by the retainer to a partially hydrated state. As described therein, a hydrogel core is formed and placed within a constraining jacket. The prosthetic disc nucleus is then dehydrated, preferably under compression within a compression mold and the entire assembly is placed in an oven. As the core dehydrates the compression mold forces the nucleus to a desired dehydrated shape in the dehydrated state. The dehydrated disc nucleus, in the dehydrated state is then placed in the retainer. The packaged disc nucleus can then be exposed to a hydration liquid where it transitions to the partially hydrated state. Once removed from the retainer, the disc nucleus, in the partially hydrated state is implanted into the disc space. U.S. Pat. No. 5,047,055 is directed to a hydrogel intervertebral disc nucleus. As described therein, a prosthetic nucleus for a disc is composed of a hydrogel material. The nucleus is made by mixing polyvinyl alcohol with a solvent heating the mixture and then poured or injected into a mold. The shaped hydrogel can be dehydrated for implantation. Other hydrogel materials are also described which can be shaped by cast molding or lathe cutting. The volume of the nucleus is said to reduce by about 80% when dehydrated and that the rigidity of the dehydrated nucleus will help the surgeons to manipulate the nucleus during an operation. U.S. Pat. No. 5,534,028 is directed to a hydrogel intervertebral disc nucleus with diminished lateral bulging and describes certain hydrogel treatment procedures which are similar to those disclosed in U.S. Pat. No. 5,047,055, e.g., see the implantation discussion at column 11, lines 25-40.

A potential shortcoming of artificial disc replacements is the propensity for extrusion of the implant through the annulus. The nucleus pulposus is held in place by the annulus in vivo. However, the annulus must be compromised in order to gain access to the diseased or damaged disc space. The resulting annular defect provides a path of least resistance through which an implant may travel under extremes of load and/or motion.

The likelihood of extrusion occurring may be increased by a poor implant cross-section to annular incision size ratio. The higher this ratio, the less likely it is that the implant will extrude. For example, if a 5 mm ø implant is placed into the disc space through a 5 mm ø incision the implant cross-section to annular incision ratio is 1.0 and extrusion is highly likely. It is therefore advantageous to keep this ratio as high as possible by reducing the incision size. This can be facilitated by decreasing the cross section of the implant which must pass through the annulus. In designing implants to be used with minimally invasive techniques, the cross-sectional area of the implant should be as small as possible. Although some of the above-described implants are dehydrated and shaped in some manner, none of them are dehydrated and reshaped so as to force the implant to assume an implantation-friendly shape substantially different from the final, hydrated implanted shape. Thus, the implant's original footprint may be maintained in the form of a wafer, which may have an aspect which is decreased along one axis, but not the other. Alternatively, isotropic shrinkage from dehydration may be effected which does not alter the topography of the implant. In the case of simple dehydration, the cross-sectional area is equal to the hydrated cross-sectional area divided by the expansion ratio.

In addition, production of dehydrated wafers requires unyielding mold fixtures made, e.g., from stainless steel in order to equalize the load while constraining the implant to a particular dimension. Water vapor must be transported from the implant in the wafer producing fixtures in order to achieve dehydration. Since metal is typically not porous, this results in long drying times, since the vapor transport path is long.

Another method of optimizing the implant cross section for minimally invasive surgery is partial hydration of a hydrogel material which allows for manipulation of the implant by the surgeon with or without specialized tools designed for this purpose. There are a number of potential drawbacks to partial hydration or plastification such as incompatibility of the plasticizer used with the sterilization method, difficulty of retaining the required amount of plasticizer within the package over extended periods and the possibility of creep occurring during storage.

The present invention addresses at least these problems by providing a spinal nucleus implant of novel configuration which has been dehydrated and reshaped in multiplanar directions utilizing a novel compression system.

SUMMARY

A spinal nucleus implant is provided which includes a substantially dehydrated hydrogel, the implant having first and second configurations, the first configuration occurring when the hydrogel is substantially dehydrated, the first configuration being substantially rod-shaped, the second configuration being substantially ellipsoid, wherein upon hydration of the substantially dehydrated hydrogel, the implant transforms from the first configuration to the second configuration. The hydrogel may be capable of anisotropic expansion. In another embodiment, the hydrogel may be capable of isotropic expansion. The rod-shaped configuration may be, e.g., can-shaped, cigar-shaped, suppository-shaped, torpedo-shaped or bullet-shaped. Both ends, or one end, of the rod-shaped implant may be blunted or tapered. The rod-shaped configuration may be substantially straight or it may be curved, e.g., to assume a boomerang-like shape. The ellipsoid configuration may, e.g., be elliptical, circular, kidney-shaped or heart shaped. In one embodiment, the ellipsoid configuration may be achieved by a combination of two or more component pieces which fit together. The spinal nucleus implant may also include at least one reinforcing mesh which can be interiorly disposed within the implant. In another embodiment, the reinforcing mesh is exteriorly disposed. In another embodiment, the implant contains at least two layers which are stacked axially, one on top of the other. In one embodiment, the length of the rod-shaped configuration is substantially equal to the major axis of the ellipsoid. In one embodiment, the hydrogel is a polyacrylonitrile copolymer. A method of implanting the spinal nucleus implant is also provided. In one embodiment, a method for minimizing the length of an incision in the annulus during insertion of a dehydrated rod-shaped spinal nucleus implant is provided wherein an incision is made in the annulus which is smaller than the diameter of the implant, and the dehydrated spinal nucleus implant is inserted through the incision thus dilating the incision, which provides a tight fit without excess incision length.

A method of shaping a spinal nucleus implant is provided which includes providing a spinal nucleus implant made, at least in part, of a hydrogel, inserting the implant into a radially collapsible member for exerting substantially equilateral circumferential compression on an object contained within the member, exerting substantially equilateral circumferential compression on the implant, thereby causing the implant to assume a rod-shaped configuration substantially corresponding to the configuration of the radially collapsible member. In one embodiment, the radial aspect of the implant is compressed while the major or axial axis maintains substantially the same length. In another embodiment, the implant is radially compressed and elongated in the axial direction as the radially collapsible member exerts substantially equilateral circumferential compression on the implant. The hydrogel may initially be fully or nearly fully hydrated and, during compression, is made to be at least partially dehydrated. This can occur by virtue of the compression, per se, or can be facilitated by regulating conditions, e.g., temperature, humidity, and/or pressure, of the atmosphere surrounding the collapsible cylinder. The collapsible member may be made of a porous elastic material made, e.g., from rubber or neoprene, or a woven or non-woven mesh or braid. The collapsible member may also be made of a metal having sufficient porosity to allow water to escape from the implant. In one embodiment, substantially equilateral circumferential compression may be exerted by stretching a collapsible sleeve in the axial direction, e.g., the distal ends of the radially collapsible member are pulled away from each other to exert such stretching. Alternatively, one end of the radially collapsible sleeve may be fixed to a stationary anchor while the other end is pulled to stretch the radially collapsible cylinder. In another embodiment, a spinal nucleus implant is placed within a collapsible member which is a cylindrical coil which is made to collapse and exert substantially equilateral circumferential compression on the implant. In another embodiment, the collapsible member is a loop is formed around the circumference of a spinal nucleus, and the loop is pulled tight to exert substantially equilateral circumferential compression on the implant. In another embodiment, a spinal nucleus implant is placed within a pressure chamber along with at least one sealed channel in communication with the implant, the sealed channel providing for egress of moisture from the implant, and pressure is exerted by gas in the pressure chamber to exert substantially equilateral circumferential compression on the implant. The implant may elongate axially through the sealed channel. In another embodiment, the collapsible member is an iris diaphragm mechanism which exerts substantially equilateral circumferential compression on a spinal nucleus implant to radially compress the implant.

In another aspect, a radially compressed xerogel spinal nucleus implant is subjected to post-compression thermoforming to remove undesirable surface irregularities and/or to reshape the radially compressed xerogel spinal nucleus implant into a final configuration. The radially compressed xerogel spinal nucleus implant is placed into a mold and subjected to sufficient heat thereby removing surface imperfections and/or reshaping the radially compressed xerogel spinal nucleus implant to a desired configuration.

DETAILED DESCRIPTION

A spinal nucleus implant ("SNI") according to the present disclosure is uniquely suited for implantation into the disc space of a diseased or damaged intervertebral disc by virtue of its ability to achieve an optimum implantable substantially dehydrated configuration and further ability to expand anisotropically or isotropically to a hydrated configuration which is adapted and configured to simulate the function of a natural nucleus propulsus. As discussed above, a small incision into the annulus lessens the possibility that a SNI will extrude through the area of the incision and also lowers the risk that the remaining annulus will be traumatized and potentially weakened. The techniques described herein provide an SNI which, in the substantially dehydrated state, has a relatively narrow substantially ellipsoid cross-section and is elongate in the axial direction so that an overall substantially rod-shaped configuration is manifest. The dehydrated SNI fits through a minimally invasive incision as a result of its small cross-section and stable structure. The SNI has a surprising capacity to expand anisotropically or isotropically from the small cross-sectional configuration into a substantially ellipsoid disc configuration which fills at least a majority of the disc space as it hydrates. As used herein, "disc" is intended to include a round, flattened structure of cylindrical dimension. In simple dehydration, the cross-sectional area is equal to the hydrated cross sectional area divided by the expansion ratio. By inducing frozen deformation according to the present disclosure, this value can be quartered and may enable further reduction by altering the shape nearer to circular, the most efficient way to pack a given volume to a minimal cross section.

Certain properties of hydrogels are utilized herein to create SNIs according to the present description. Many materials may be induced to exhibit an alteration of shape by altering some aspect of the material. For example, a snowball can be fashioned from snow flakes and the snowball will retain its shape indefinitely if maintained at the same environment. Once the temperature is increased, however, the snowball returns to liquid water. Many hydrogel polymers behave in a similar manner, which is to say they can be deformed, frozen into a deformed shape and they can maintain that shape indefinitely or until, e.g., a temperature change causes the polymer to "relax" into the shape originally held prior to freezing. This property is often referred to as shape memory or frozen deformation by those skilled in the art.

The temperature at which frozen deformation occurs is referred to as the glass transition temperature or $T_g$. At $T_g$ several polymer properties such as density, entropy and elasticity may sharply change. Many polymers can be mixed with agents that can have a drastic effect on a polymer $T_g$. Polymers which absorb fluid are of particular interest and water is the preferred $T_g$ altering agent. Hydrogels which contain less than about five percent water may be considered dehydrated or xerogels. The $T_g$ of a xerogel will change as it absorbs fluids containing water. Once the $T_g$ becomes lower than ambient the now partially hydrated hydrogel becomes pliant and may be elastically deformed. If the polymer is held in a state of elastic deformation while the $T_g$ is raised above ambient the polymer will maintain the deformed state indefinitely. This can be accomplished by either lowering the ambient temperature (freezing) or by returning the polymer to its xerogel state thus raising the $T_g$.

Using this method, hydrogel articles may be produced with vastly differing xerogel shapes compared to hydrated shapes. This is especially useful in cases such as medical implants where, in delivering a prosthesis into the human body, every care should be taken to reduce trauma to the patient. An implant which is shaped as an ellipsoidal cylindrical disc, for instance, is re-shaped, in accordance with the present invention, into a tapered elongate rod in order to facilitate minimally invasive implantation. Once the implant is indwelling and has absorbed water containing liquids it will substantially return to the shape of the disc and maintain that shape indefinitely. As used herein, "substantially" is intended to mean any of "approximately", "nearly" or "precisely."

Suitable polymers for use in fabricating an SNI herein may contain one or more polymeric components. Preferably, such polymers are made of polymeric components having a C-C backbone. Suitable polymers, such as polyvinylalcohol, polyvinyl pyrrolidone or derivatives of polyacrylic or polymethacrylic acid, are more resistant to biodegradation than polymers with heteroatoms in their backbones, such as polyurethanes or polyesters. Preferably, at least one of the polymeric components contains both hydrophilic and hydrophobic groups.

A preferred polymer configuration includes two polymer phases of different hydrophilicity, the less hydrophilic phase having higher content of hydrophobic groups and more hydrophilic phase having higher content of hydrophilic groups. The less hydrophilic phase is preferably crystalline and more hydrophilic phase is preferably amorphous, as can be established from X-ray diffraction.

Advantageous hydrophobic groups are pendant nitrile substituents in 1,3 positions on a polymethylene backbone, such as poly(acrylonitrile) or poly(methacrylonitrile). The hydrophilic phase may preferably contain a high concentration of ionic groups. Preferred hydrophilic groups are derivatives of acrylic acid and/or methacrylic acid including salts, acrylamidine, N-substituted acrylamidine, acrylamide and N-substituted acryl amide, as well as various combinations thereof. A particularly preferred combination contains approximately two thirds acrylic acid and its salts (on molar basis), the rest being a combination of plain and N-substituted acrylamides and acrylamidines.

At least one polymeric component is preferably a multiblock copolymer with alternating sequences of hydrophilic and hydrophobic groups. Such sequences are usually capable of separating into two polymer phases and form strong physically crosslinked hydrogels. Such multiblock copolymers can be, for example, products of hydrolysis or aminolysis of polyacrylonitrile or polymethacrylonitrile and copolymers thereof. For convenience, polymers and copolymers having at least about 80 molar % of acrylonitrile and/or methacrylonitrile units in their composition may be referred to as "PAN". Hydrolysis and aminolysis of PAN and products thereof are described, for example, in U.S. Pat. Nos. 4,107,121; 4,331, 783; 4,337,327; 4,369,294; 4,370,451; 4,379,874; 4,420,589; 4,943,618, and 5,252,692, each being incorporated herein by reference in their respective entireties.

The SNI can include at least two polymeric components arranged as an interpenetrating network. In that case, one component is essentially a hydrophobic polymer capable of forming a reticulated crystalline fibrillar mesh or scaffold. Examples of such polymers are polyurethane, polyurea, PAN, expanded polytetrafluoroethylene, cellulose triacetate and polyvinylalcohol. The spaces between the fibrils may be filled by a continuous phase of hydrophilic polymer with a 3-dimensional physical or covalent network (i.e., a hydrogel such as crosslinked polyvinylalcohol or polyvinylpyrrolidone). The most suitable hydrogels for this role are those based on hydrophilic derivatives of polyacrylic and polymethacrylic acid.

A preferred material for the SNI is a synthetic composite of a cellular (or domain) type with continuous phase formed by a hydrophobic polymer or a hydrophilic polymer with low to medium water content forming a "closed cell" spongy structure that provides a composite with good strength and shape stability. Examples of suitable polymers are polyurethanes, polyureas, PAN, polydimethylsiloxanes (silicone rubber), and highly crystalline multiblock acrylic and methacrylic copolymers. The polymer should be sufficiently permeable to water. It is known that even distinctly hydrophobic polymers, such as silicone rubber, can form swellable composites. More preferably, the continuous phase is formed by a strong hydrophilic polymer with sufficient permeability for water but impermeable to high-molecular solutes. Examples of such polymers are highly crystalline hydrogels based on segmented polyurethanes, polyvinylalcohol or multiblock acrylonitrile copolymers with derivatives of acrylic acid. Typically, suitable polymers for the continuous phase in cellular composites have a water content in fully hydrated state between about 60% by weight and about 90% by weight, preferably between about 70% and about 85% by weight.

The second component may be a highly hydrophilic polymer of high enough molecular weight to prevent permeation of the hydrophilic polymer through the continuous phase. This component is contained inside the matrix of the continuous phase. The entrapped hydrophilic polymers (the so-called "soft block") may be high-molecular weight water-soluble polymers, associative water-soluble polymers or highly swellable hydrogels containing, in fully hydrated state, at least about 95% of water and up to about 99.8% of water. Such hydrogels are very weak mechanically. However, it does not matter in composites where such polymers' role is generation of osmotic pressure rather than load-bearing, with compression strength in full hydration in the range of about 0.01 MN/m$^2$ or lower.

A system with closed cells (or domains) containing highly swellable or water-soluble polymers can form composites with very high swelling pressure as needed for the SNI function. Examples of suitable hydrophilic polymers are high-molecular weight polyacrylamide, polyacrylic acid, polyvinylpyrrolidone, polyethyleneoxide, copolymers of ethyleneoxide and propyleneoxide or hyaluronic acid; covalently crosslinked hydrogels such as hydrophilic esters or amides of polyacrylic or polymethacrylic acids; and physically crosslinked hydrogels, such as hydrolyzates or aminolyzates of PAN.

Particularly suitable are associative water-soluble polymers capable of forming very highly viscous solutions or even soft physical gels. Preferred are associative polymers containing negatively charged groups, such as carboxylates, sulpho-groups, phosphate groups or sulfate groups. Particularly preferred are associative polymers formed by hydrolysis and/or aminolysis of PAN to high but finite conversions that leave a certain number of nitrile groups (typically, between about 5 and 25 molar %) unreacted.

Preferred composites have both a continuous phase and a dispersed phase formed by different products of hydrolysis or aminolysis of PAN. In this case, both components are compatible and their hydrophobic blocks can participate in the same crystalline domains. This improves anchorage of the more hydrophilic component and prevents its extraction or disassociation. The size of more hydrophilic domains may vary widely, from nanometers to millimeters, preferably from tens of nanometers to microns.

The ratio between the continuous discrete phase (i.e., between more hydrophobic and more hydrophilic components may vary from about 1:2 to about 1:100 on a dry weight basis, and a preferred ratio ranges from about 1:5 to about 1:20. Examples of compositions and implants are described in U.S. Pat. Nos. 6,264,695 and 6,726,721, both of which are incorporated herein by reference in their entireties. A preferred method of making the composite is described in U.S. Pat. No. 6,232,406, herein incorporated by reference in its entirety.

The SNI may consist of a single layer or, in a preferred embodiment, the SNI may be composed of at least two substantially parallel (when the SNI is hydrated) soft layers of an elastically deformable hydrogel and at least one rigid layer, the rigid layer having less compressibility than the soft layers, being adjacent to the soft layers, parallel to them, and firmly attached to them. In some embodiments, the soft layers have the same thickness and/or composition. In other embodiments, the soft layers may have different thickness and/or composition. The SNI may have more than one rigid layer. The rigid layers may have the same or different thickness and/or composition. In one embodiment, the number of soft layers is one more than the number of rigid layers, with, e.g., at least three soft layers. In a preferred embodiment, an interiorly disposed reinforcing member is present. The reinforcing member may be a fabric, foil, net or mesh and may also have a configuration which corresponds to the hydrated shape of the SNI, e.g., a flat ellipsoid configuration when the SNI is hydrated. Alternatively, the reinforcing member may be exteriorly disposed, e.g., a jacket which surrounds all or part of the SNI. The fabric, foil, net, mesh or jacket may be constructed from relatively durable materials including but not limited to metal foil, metal fibers, polymeric fibers such as polyethylene terephthalate, polyamide, polyurethane, polyureas, acrylic and methacrylic polymers, expanded polytetrafluoroethyl (Goretex), graphite, etc. These materials can be used either alone, or in a composite form in combination with elastomers or hydrogels. Especially advantageous are mesh, woven, non-woven, perforated, or porous formats of these materials which will allow solid anchoring of the soft layer.

Methods of manufacturing SNIs are disclosed, e.g., in U.S. Pat. Nos. 6,264,695 and 6,726,721. Examples of particularly suitable hydrogel forming copolymers are prepared by a partial alkaline hydrolysis of polyacrylonitrile ("HPAN") in the presence of sodium thiocyanate (NaSCN). The resulting hydrolysis product is a multi-block acrylic copolymer, containing alternating hydrophilic and hydrophobic blocks. Hydrophilic blocks contain acrylic acid, acrylamidine, and acrylamide. In one embodiment, for example, a PAN hydrolysate polymer (referred to herein HPAN I) (46±1% conversion of hydrolysis) having the following composition: acrylonitrile units ~53-55%, acrylic acid units ~22-24%, acrylamide units ~17-19%, acrylamidine units ~4-6%, as determined by $^{13}C$ NMR, is dissolved in a suitable solvent such as a ~55% solution of sodium thiocyanate in water to form a viscous solution. The viscous solution is poured into a porous mold having, e.g., a cylindrical shape. The solution can then be solvent cast, e.g., by solvent exchange (e.g., water for NaSCN). The pores should be sufficiently small as to not permit the polymer to diffuse or leak out of the mold.

If additional layers are desired, e.g., a more rigid layer is then placed on top of the viscous HPAN I solution. The more rigid layer may be a preformed hydrogel such as another PAN hydrosylate polymer, referred to herein as HPAN II (28±1% conversion of hydrolysis), having the following composition: acrylonitrile units ~71-73%, acrylic acid units ~13-15%, acrylamide units ~10-12%, acrylamidine units ~2-4%, as determined by $^{13}C$ NMR, dissolved in ~55% NaSCN which was solvent cast, washed, dried and cut to a suitable shape for fitting over the viscous HPAN I solution in the mold. In certain embodiments, the HPAN II layer may include a reinforcing member which was included during solvent casting. In other embodiments, the reinforcing member may be placed over the viscous solution in the mold prior to placing the preformed more rigid layer in the mold.

After the more rigid layer is placed over the viscous solution, if desired, additional viscous polymer solution is added to the mold until a desired thickness is reached. And if desired, another preformed, dried hydrogel layer, with or without the reinforcing member, is placed over the viscous solution, followed by another layer of viscous polymer solution. The process may be repeated until any desired number of layers is formed. The order of layering may be varied to suit particular applications. After the last layer is applied, the mold is closed and placed in water for solvent exchange. For example, the sodium thiocyanate solution diffuses out and is replaced with water, causing the viscous solution to coagulate. In the case of successive layers of HPAN I and HPAN II, the layers adhere to each other without the need for any adhesives. In certain embodiments, the interface between the HPAN I layers and the HPAN II layers is blurred by comingling of the polymers during the manufacturing process, leading to a gradual transition from layer to layer. In other embodiments, adhesives such as polyurethanes or cyanoacrylates are used to bond the layers together.

Upon completion of the solvent exchange extraction process SNI are hydrated to their fullest extent (~90% equilibrium-water content (EWC)). In this fully hydrated state the SNI is readily deformed under modest loads and the hydrogel, e.g., HPAN I OR HPAN II, glass transition temperature ($T_g$) is well below room temperature. This is the "relaxed" state of the SNI, the state to which it will return after loading below the critical level. The critical level is the point at which permanent deformation occurs and is further discussed below. In accordance with the present invention, the fully hydrated SNI is deformed into a desirable second shape and the temperature of the SNI is lowered below its $T_g$ (near freezing point of water). Such an SNI would be said to be in a state of "frozen deformation" and it would retain that deformed shape indefinitely. Once the SNI is warmed above its $T_g$, however, the SNI would recover to its original memorized configuration.

The $T_g$ of the hydrogel increases with decreasing water content. This characteristic is exploited by simultaneously raising the $T_g$ while deforming the SNI into a desired shape. In other words, as the SNI dehydrates it is freezing the position of the polymer chains. To regain the original shape of the SNI, the $T_g$ may be lowered by hydration.

In order to obtain a preferred rod-shape having a cross-sectional ellipsoid shape for implantation, e.g., suppository, bullet, tapered cylinder, etc., from, e.g., an elliptical or circular footprint SNI, deformation is advantageously maintained radially, substantially parallel with the major elliptical axis or diameter. This is accomplished by placing the implant within a radially collapsible member for exerting substantially equilateral circumferential compression on an object, e.g., an SNI, contained within the member. Suitable radially collapsible members include, e.g., a flexible sleeve such as a braided sock, a flexible coil, iris diaphragm, collapsible loop, etc. In a preferred embodiment, the radially collapsible member is porous or semipermeable so that water, either as liquid or as vapor, passes through the member. The collapsible member may be made of an elastic material such as rubber or neoprene fabric which has been made porous by any technique known to those skilled in the art, or a woven or non-woven mesh or braid. The collapsible member may also be made of a flexible metal having sufficient porosity to allow water to exit from the implant. The collapsible member does, however, need to be stiff enough to be able to exert sufficient compressive force when tension is applied, as described below, to compress the SNI, i.e., it should not be so elastic that it deforms without being able to exert sufficient compressive force.

Figure 1A:
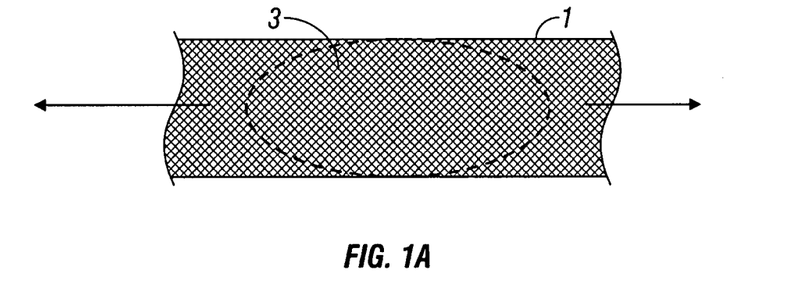
FIG. 1A is a schematic top view illustration of a spinal nucleus implant positioned in a radially collapsible cylinder during dehydration.
Figure 1B:
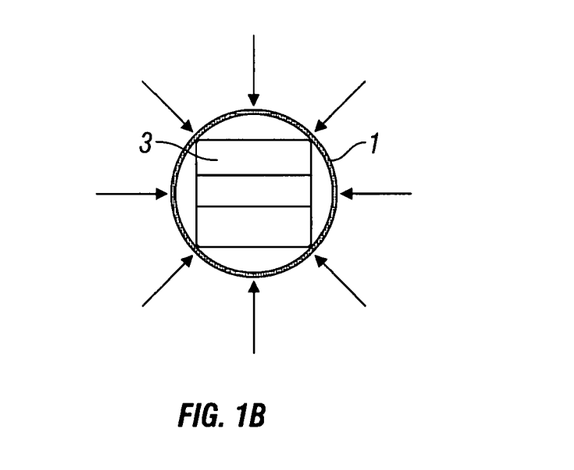
FIG. 1B is a schematic cross-sectional illustration of the spinal nucleus implant positioned in a collapsible cylinder shown in FIG. 1 with vectors illustrating radial compression exerted by the collapsible cylinder on the spinal nucleus implant.
Figure 2:
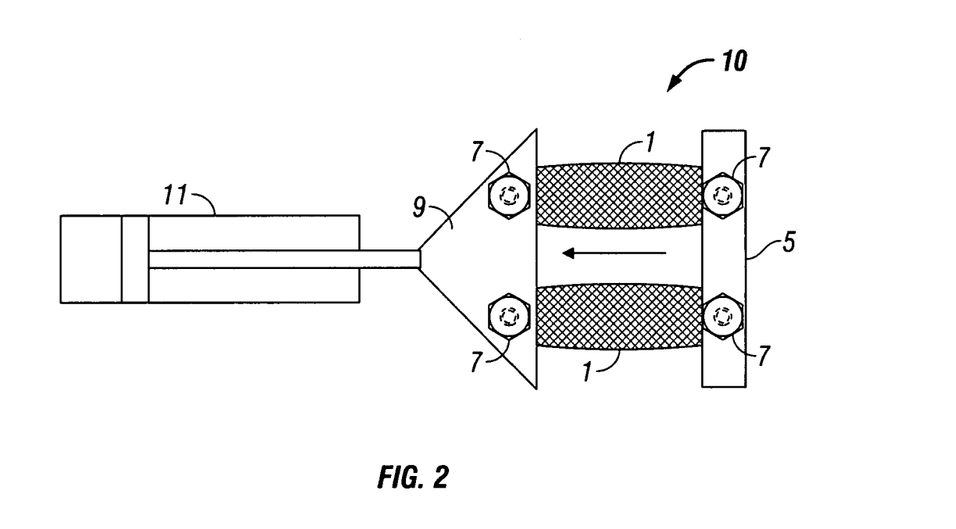
FIG. 2 is a schematic illustration of an example of a tensioning device attached to a stretching rack. Two radially collapsible cylinders are attached to the rack. A vector shows the direction of pulling force on the rack.
Figure 3:
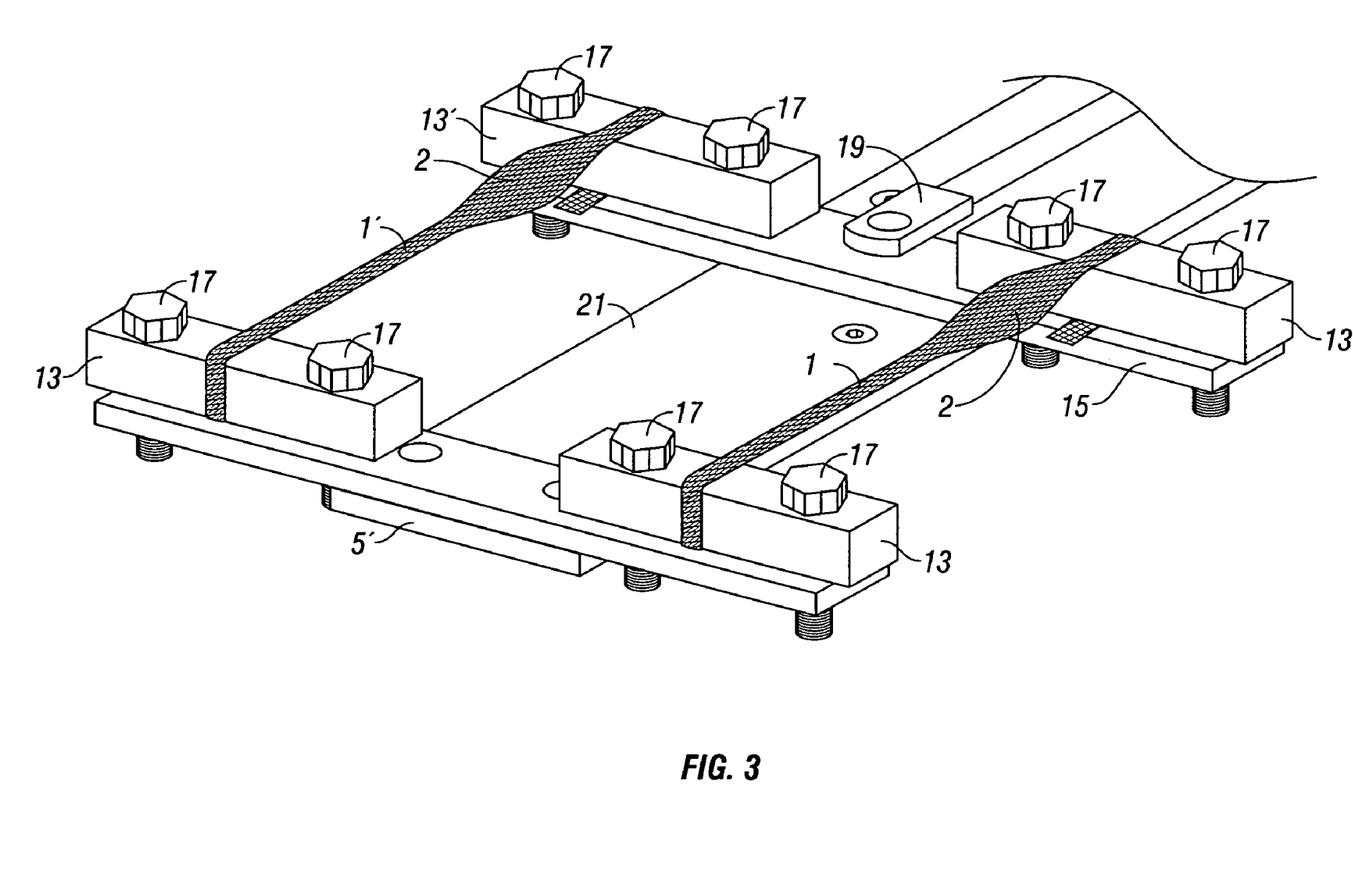
FIG. 3 is an perspective view of two radially collapsible members, in this case, braided sleeves, attached to a stretching rack. A central bulge is evident where spinal nucleus implants are respectively contained within the sleeves.
Figure 4A:
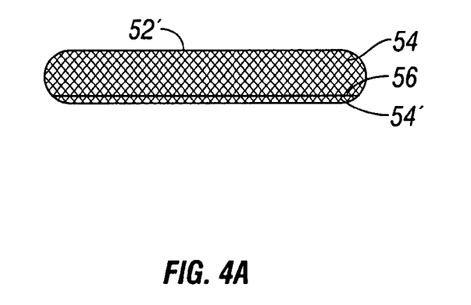
FIG. 4A is a top view of a spinal nucleus implant dehydrated in accordance with the present disclosure to assume an elongate rod-shaped configuration having tapered ends.
Figure 4B:
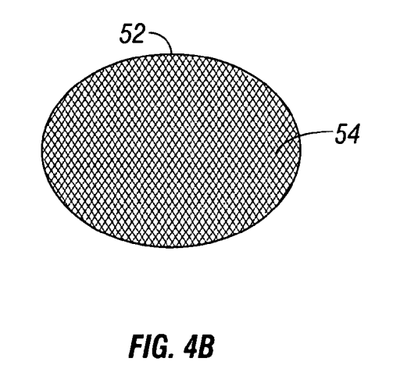
FIG. 4B is a top view of a spinal nucleus implant having an ellipsoid disc configuration after hydration. The dehydrated implant shown in FIG. 4A assumes the shape of the hydrated implant upon hydration.
Figure 4C:
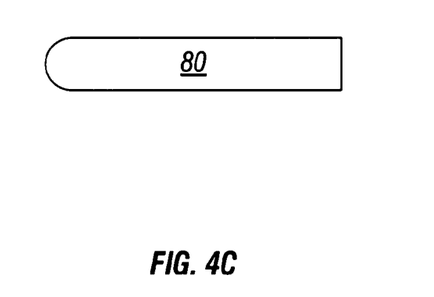
FIG. 4C is a side view of a spinal nucleus implant having one blunted end.
Figure 4D:
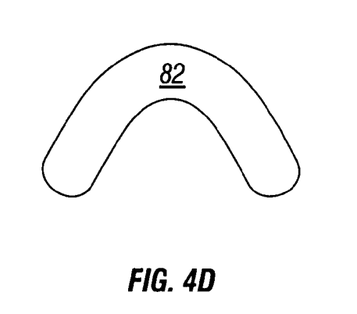
FIG. 4D is a top view of a spinal nucleus implant having a boomerang-like shape.
Figure 5A:
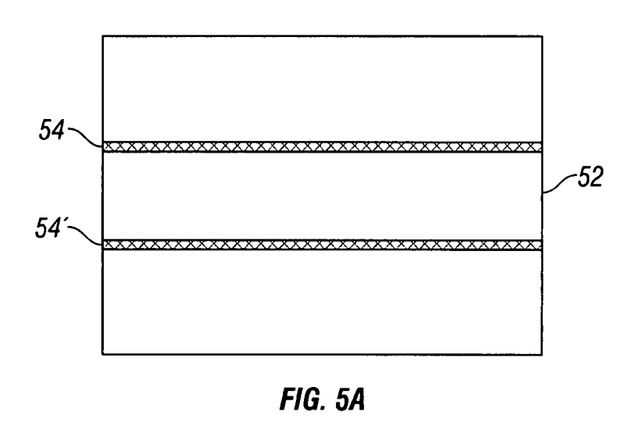
FIG. 5A is an image depicting a side view of the hydrated spinal nucleus implant shown in FIG. 4B.
Figure 6:
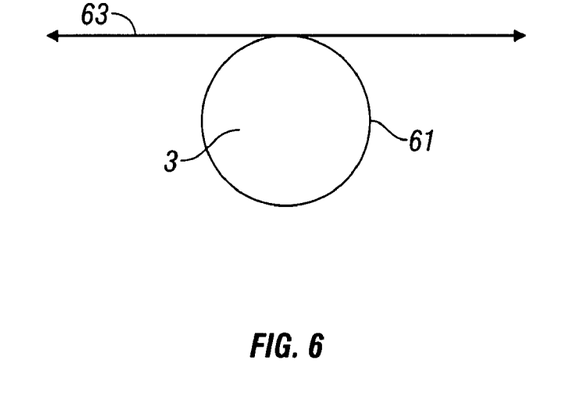
FIG. 6 illustrates a loop-type radially compressive member.

In operation, the radially collapsible member exerts substantially equilateral circumferential compression on the implant by substantially uniformly decreasing in diameter while contacting the implant. The preferred porous nature of the collapsible member allows water from the implant to escape into the surrounding environment so that the implant can become dehydrated. In one embodiment, the sleeve radially collapsible member is stretched in length which causes the inner diameter to decrease. See, FIGS. 1A, 1B, 2 and 3. FIG. 1A shows a radially collapsible cylinder 1 containing a spinal nucleus implant 3. FIG. 1B depicts radially compressive force vectors (arrows) exerted by the radially collapsible cylinder 1 on the SNI 3. FIG. 2 depicts a schematic diagram of a stretching rack 10 and a tensioning device 11 which includes a fixed support 5 having radially collapsible cylinder retainers 7 which engage the radially collapsible cylinders. A movable support 9 engages the radially collapsible cylinders a distal end through the retainers 7. The movable support 9 communicates with the tensioning device 11 which exerts a pulling force on the movable support 9 in the direction of the vector arrow. FIG. 3 depicts another embodiment of a stretching rack wherein the radially collapsible cylinder 1' is a braid. Contained within each of the respective collapsible cylinders 1 is a SNI, represented by bulges 2. The radially collapsible cylinder 1' is fastened to the fixed support 5' by retainer bars 13. The radially collapsible cylinder 1' is fastened to movable tensioning member 15 by retainer bars 13'. Retainer bars 13 and 13' are fastened to the fixed support and the movable tensioning member 15, respectively, by bolts 17. Arm 19 communicates between the movable tensioning member 15 and a tensioning device (not shown). The movable tensioning member 15 is maintained on substantially the same plane as the fixed support 5' by guide 21. FIG. 4A depicts a bullet-shaped radially compressed, dehydrated SNI 52', after treatment as described herein. The dehydrated implant 52' contains interiorly disposed reinforcement members 54 and 54' in a collapsed configuration. The collapsed and juxtaposed edges of the reinforcement members 54 and 54' are depicted as combined edge 56. When the dehydrated SNI 50 is hydrated, it expands and becomes a disc shaped hydrated SNI 52 as shown in FIG. 4B. FIG. 4C depicts a side view of a dehydrated SNI 80 having one end that is blunted. FIG. 5A depicts a side view of the hydrated SNI 52. Reinforcing members 54 and 54' are interiorly disposed in the SNI 52. In another embodiment, a coil radially collapsible member is used to exert radial compression by decreasing the interior diameter of the coil. For example, by fixing the inside end of the coil and pulling on the outermost end of the coil, the diameter of the coil is decreased, thereby exerting equilateral compression force on the circumference of the implant. The width of the coil can vary but is advantageously longer than the final elongated length of the compressed dehydrated implant. In another embodiment illustrated in FIG. 6, the radially collapsible member is a loop 61 created around the implant 3 which is tightened and made to decrease in diameter by tensioning a string 63 which either constitutes the loop or is attached to the loop. Both ends, or one end, of the string 63 shown in FIG. 6 may be tightened to exert radially compressive force on the object contained within the loop. The loop may be made of a single strand, or of a fabric wide enough to cover the length of the implant when it is compressed and dehydrated. In one embodiment, a lasso-like knot configuration can be utilized to exert radially compressive force. Alternatively, a shoe-lace-like configuration can be utilized to exert radially compressive force. In another embodiment, the radially collapsible member is an iris diaphragm having a collapsible aperture utilized to exert radial compression on the implant. Methods of manufacturing such diaphragms are well known. The blades of the iris should be sufficiently thick enough to cover the elongated dehydrated implant after radial compression. In one embodiment, a plurality of iris diaphragms are placed coaxially adjacent one another to form an extended collapsible aperture. A small amount of space between each allows water to dissipate into the atmosphere. The decrease in diameter provided by the above-described embodiments is responsible for applying load equally along the outer circumference of the SNI.

As mentioned above, in one embodiment, the collapsible member is a flexible sleeve. The materials which make up the sleeve and the shape of the sleeve used to apply radial load to the SNI may be varied and are important to the process. In a preferred embodiment, the sleeve should be made of a fairly inelastic material such as PET, nylon, metal thread, etc.; should be composed of relatively small fibers; and the weave should be tight in terms of number of fibers per filament. Standard electrical wire wrap, for instance is composed of monofilament large diameter fibers of nylon. While these perform well in applying radial stress the weave is so loose that the outer layers of a hydrogel, e.g., HPAN I extrude into the weave producing a rough surface finish. A high quality polyethylene terephthalate (PET) sleeve with small polyfilament fibers has a very tight weave and leaves a much smoother surface. A textile fabric of high thread count, for example, Easy Cut™ braided polyester mesh sleeving, available from McMasster-Carr Supply Company, made, e.g., of PET, which is most preferred. There is, however, a tradeoff in terms of expansion ratio versus filament diameter which should be considered when choosing a suitable sleeve collapsible member. The textile fabric may be woven or non-woven as well. The weave of the fibers allows water to exit the implant and enter the surrounding environment during compression and dehydration. Similar considerations are involved in choosing the materials which make up the coil and loop embodiments described above. The coil may be made of a solid, though porous or semi-permeable membrane of, e.g., rubber, neoprene or the like, or it may be woven or non woven fabric or mesh. The iris diaphragm must have blades which are sufficiently rigid to exert sufficient force on the implant without bending. Metal, e.g., stainless steel, brass, nickel, titanium and the like, or polymeric materials, e.g., nylon, polyethylene, polyethylene terephthalate and the like are suitable. Selection of these and other suitable materials are well within the ordinary skill in the art.

The dimensions of the collapsible member are important, but may be adapted to by altering tension or drying time. The dimensions also depend on the final size/cross section desired with the general rule being smaller extended member diameters produce more rounded SNIs whereas larger member diameters produce a squarer SNI cross section.

The collapsible member is loaded in tension via any tensioning device known to one skilled in the art, e.g., a pneumatic cylinder, a hydraulic cylinder, springs, weights, pulleys, etc. The tension on the collapsible member can be precisely controlled by regulating the pressure within the tensioning device, translating into constant, controlled radial load on the SNI. In the case of a sleeve collapsible member, once the SNI is loaded into the collapsible member and the collapsible member is tensioned, three things occur: the SNI dehydrates, the SNI deforms, the collapsible member extends. By varying the tension on the collapsible member, the length of the SNI can be extended, thereby decreasing the minor axis and height. This can also be controlled, to some extent, by the speed of dehydration (temperature, pressure and humidity), with longer dehydration time producing longer SNI length and vise versa.

There are two concerns with respect to drying time and collapsible member tension that should be considered. The first is creep, which may set in if the dehydration time is extended unreasonably long (over several days). The second is permanent deformation which may occur if excessive stress is applied to the implant. Both of these concerns only occur at critical point extremes which are to be avoided. Permanent deformation may occur in the hydrogel implant if the soft-block domains of the polymer are displaced to a point where they cannot reorient themselves into the original lattice configuration, i.e., the memorized shape. This can happen, e.g., by either deforming the original shape so severely that many of the bonds which hold the soft-blocks in place are severed, or by heating the implant sufficiently above the $T_g$ to cause the soft-block domains to permanently or irrevocably assume a new configuration outside of the originally contemplated structure, which causes an undesirable change in shape. Thus, the melting point of the soft block should not be exceeded. The melting point of the soft block may vary based on the amount of water content. Such melting points may be determined by conventional techniques known to those skilled in the art. For example, at 18% hydration of HPAN I, permanent deformation is manifest at temperatures over 105° C.

The fixture that tensions the collapsible member can be any tensioning device known to those skilled in the art. For example, a tensioning device driven by a pneumatic cylinder which is connected to clamps which hold the ends of the collapsible member, e.g., a sleeve. Pneumatics or hydraulics may be preferred over springs largely due to the ability of pneumatics or hydraulics to apply a constant load over relatively long distances compared to springs. Since there may be some variability in where a member is clamped, the drying rate of the SNI or the ratio of height to diameter during dehydration, a yoke 5 can be employed to equally split the applied tension between two or more collapsible members. In this embodiment (see, e.g., FIGS. 2 and 3), an important component of the tensioning fixture is the compressed air regulator. The pressure applied to the pneumatic cylinder is proportional to the tension the collapsible member, e.g., sleeve, coil, loop, etc. receives, regardless of length. Each SNI size requires a different pressure setting. The amount of pressure required may range of from about 40 to about 175 pounds per square inch on a 1.25" piston in the case of a SNI made from HPAN I/HPAN II hydrogels. A schematic representation of a tensioning device incorporating the sleeve collapsible member is illustrated in FIG. 2. It should be understood that any suitable tensioning device, e.g., pneumatic, hydraulic, springs, levers, pulleys, etc. may be utilized by those skilled in the art.

Figure 7:
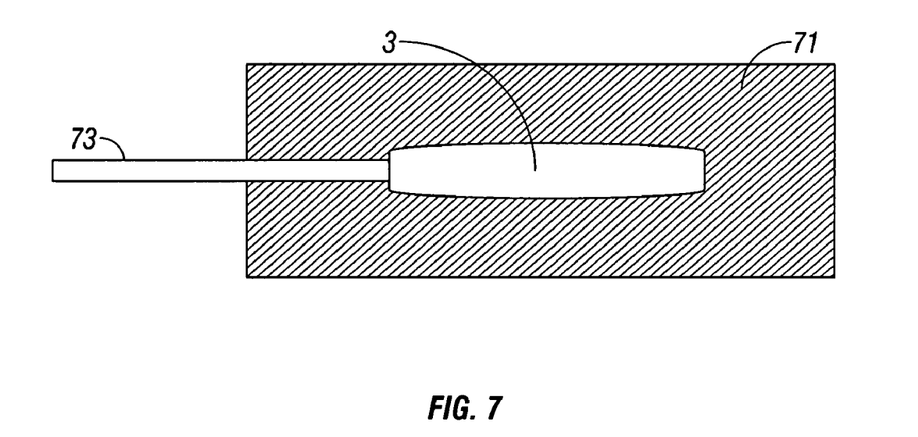
FIG. 7 is a schematic illustration of a spinal nucleus implant in a pressure vessel containing a channel in communication with the implant.

In another embodiment for exerting substantially uniform radially compressive force, a SNI is placed within a pressure chamber containing at least one sealed channel in communication with the implant, the sealed channel providing for egress of moisture from the implant. Pressure is exerted by gas in the pressure chamber to exert substantially equilateral circumferential compression on the implant. The sealed channel also allows the implant to elongate axially therethrough. The SNI may optionally be substantially sealed within a membrane which may or may not be permeable to the working gas. At least one channel is attached to the membrane and is held at a lower pressure than the working gas. The working gas may be simple atmospheric pressure (with the channel held at vacuum) or may be any compressed gas. The working gas exerts pressure equally over the surface of the membrane which loads the SNI within. Water vapor is transported out of the membrane either through the capillary or directly through the membrane. The sealed channel can be used as a guide to create the cross-sectional shape and diameter of the end of the dehydrated, compressed SNI. Two sealed channels can be placed distally at each end of the major axis or diameter of the SNI to provide more uniform elongation of the implant as it dehydrates and compresses. FIG. 7 schematically illustrates a pressure vessel 71 with one sealed channel 73 in communication with an SNI 3.

In general and in a preferred embodiment, the majority of the dehydration process should occur at room temperature over an extended period of time (e.g., 18 to 36 hours). The SNI can be monitored to determine the extent of dehydration and the time period adjusted accordingly. Relative humidity, air circulation, air pressure and room temperature should be controlled during this period. Especially preferred conditions are about 21° C. at 50% relative humidity under moderate airflow. Once the SNI has reached <~30% water content it may be forced dry at elevated temperature, e.g., from about 25° C. to about 105° C. for typically less than about 24 hours to rapidly remove remaining water. As above, the state of dehydration may be monitored to determine if greater or lesser amounts of time are needed. When the SNI is completely dehydrated, the implant is fairly rigid in its state of frozen deformation. Alternatively, a slight degree of hydration provides some flexibility to the implant. The less dehydrated, the more flexible. It is contemplated herein that "substantially dehydrated" preferably encompasses from about 12% or less, to about 30% water by weight of the implant.

Upon completion of forced dehydration, the SNI is extremely stable in terms of shelf life, providing that it is kept dry. Even brief exposure to humidity during the sterilization process should not have significant effects. Temperatures above about 80° C. should be avoided for extended periods as this may bring the implant above its $T_g$ if it has absorbed some small amount of water vapor.

Figure 5B:
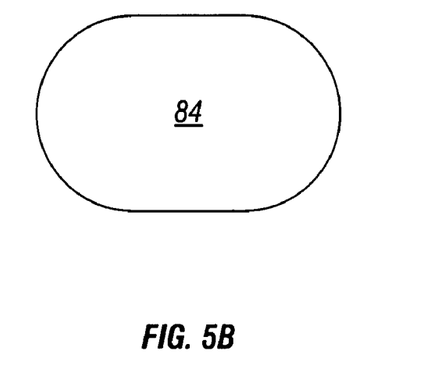
FIG. 5B is a top view of a spinal nucleus implant having an elliptical shape.
Figure 5C:
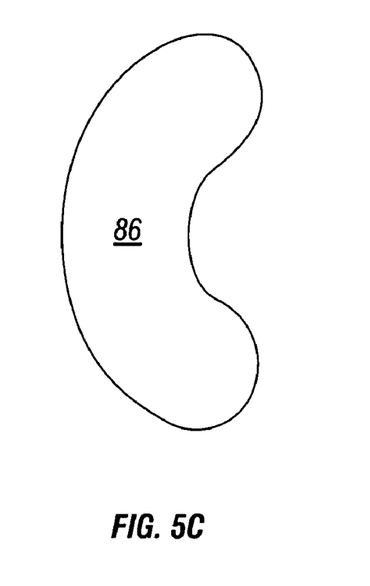
FIG. 5C is a top view of a spinal nucleus implant having a kidney shape.
Figure 5D:
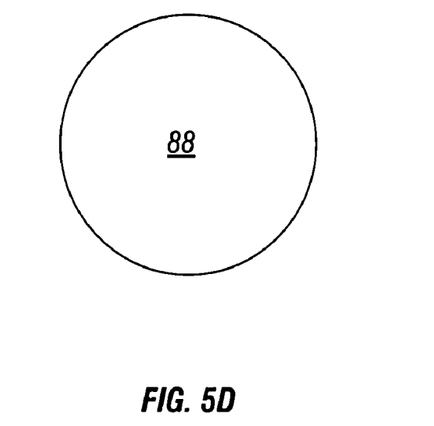
FIG. 5D is a top view of a spinal nucleus implant having a circular shape.
Figure 5E:
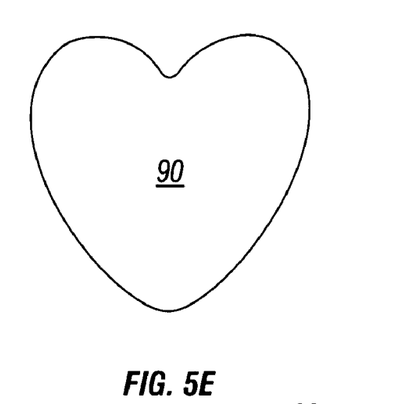
FIG. 5E is a top view of a spinal nucleus implant having a heart shape.
Figure 5F:
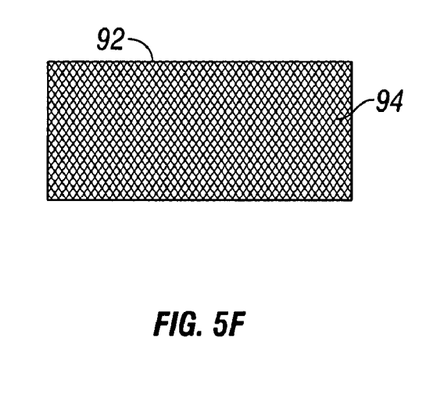
FIG. 5F is a side view of a spinal nucleus implant having an exteriorly disposed reinforcing member.
Figure 5G:
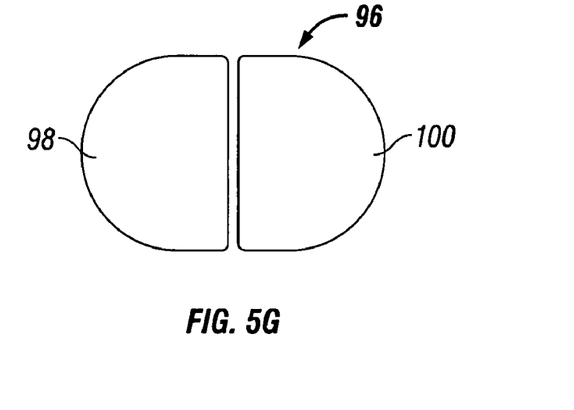
FIG. 5G is a top view of a spinal nucleus implant made of two complimentary components.

It is contemplated that the dehydrated implant would have a substantially rod-shaped configuration. As mentioned above, the rod-shaped configuration may be, e.g., can-shaped, cigar-shaped, suppository-shaped, torpedo-shaped, bullet-shaped, etc. Both ends, or one end, of the rod-shaped implant may be blunted or tapered. The rod-shaped configuration may be substantially straight or it may be curved, e.g., to assume a semi-circle or boomerang-like shape or a wiggle shape. FIG. 4B depicts a top view of a boomerang-like shaped SNI 82. Such shape alterations may be implemented by shaping, molding or bending the rod-shaped implant during the dehydration process. The final configuration may be determined on a case by case basis depending on the configuration of the defect in the disc space. The ellipsoid disc configuration of the hydrated implant may, in preferred embodiments, be elliptical (FIG. 5B), heart-shaped (FIG. 5E), kidney-shaped (FIG. 5C) or circular (FIG. 5D). The height of the ellipsoid disc may range, e.g., from 3 mm to 18 mm. FIGS. 4A, 4B and 5A depict images of a radially compressed dehydrated rod-shaped SNI 50 having blunted ends for implantation and, after hydration, an expanded hydrated elliptical SNI 52. Two internally disposed reinforcing members 54, 54' may be, e.g., substantially parallel. See, e.g., FIG. 5A. FIG. 5F depicts a side view of an SNI 92 having an exteriorly disposed reinforcing member 94. In one embodiment, the ellipsoid configuration may be achieved by a combination of two or more component pieces which fit together. See, e.g., FIG. 5G showing a top view of a first component piece 98 which compliments a second component piece 100 to form an ellipsoid SNI 96. In that case, the corresponding dehydrated SNIs are inserted sequentially so that upon hydration, they fit together to fill, or substantially fill, the disc space.

Surface irregularities may be present on a dehydrated compressed implant which was compressed as described above by a radially collapsible member by virtue, e.g., of some extrusion of the hydrogel through pores or through interstitial spaces of the member. For example, a woven or non-woven collapsible sleeve may have interstitial spaces that allow hydrogel to extrude therein under compressive force. In addition, after radial compression, as described above, the dimensions of the implant may be different than the ultimate dimensions desired by the practitioner. Both of these instances can be remedied by post-compression thermoforming of the SNI. In this aspect, a dehydrated, compressed SNI is placed within a mold which may be advantageously pre-heated to about 70-150° C., but more preferably, closer to the melting point of the polymer, e.g., about 105° C. Care must be taken to avoid subjecting the SNI to excess heat which causes the hydrogel to exceed its critical point, and thus causing permanent deformation of the SNI. If the temperature is high, the SNI must be quickly removed from the mold to avoid permanent deformation. The mold is machined to the exact desired final dimensions of the xerogel SNI and essentially irons out surface roughness to a substantially smooth surface, which is less abrasive to surrounding tissue when implanted. If desired, and if the xerogel implant is compressed by a radially compressive member or by gas compression, but has not achieved, e.g., an ideal enough straight rod-like configuration, or if the ends are not sufficiently blunted or otherwise tapered, post-compression thermoforming may be utilized to fine tune the shape as well as remove any surface irregularities which may be present. Post-compression thermoforming may also be utilized to bend an SNI to a desired configuration, e.g., to a boomerang shape.

A radially compressed, dehydrated SNI according to the disclosure herein may contain a medicinal agent. "Medicinal agent" is used in its broadest sense and it includes any substance or mixture of substances which may have any clinical use. It is to be understood that medicinal agent encompasses any drug, including hormones, antibodies, therapeutic peptides, etc., or a diagnostic agent such as a releasable dye which has no biological activity per se. Thus, in its broadest aspect, a method of delivery herein may be defined as the release of any substance, which may or may not exhibit biological activity.

Examples of medicinal agents that can be used include anticancer agents, analgesics, anesthetics, anti-inflammatory agents, growth factors, antimicrobials, and radiopaque materials. Such medicinal agents are well-known to those skilled in the art. The medicinal agents may be in the form of dry substance in aqueous solution, in alcoholic solution or particles, microcrystals, microspheres or liposomes. An extensive recitation of various medicinal agents is disclosed in Goodman and Gilman, The Pharmacological Basis of Therapeutics, 10th ed. 2001, or Remington, The Science and Practice of Pharmacy, 21 ed. (2005), the disclosures of which are hereby incorporated by reference. As used herein, the term "antimicrobial" is meant to encompass any pharmaceutically acceptable agent which is substantially toxic to a pathogen. Accordingly, "antimicrobial" includes antiseptics, antibacterials, antibiotics, antivirals, antifungals and the like. Radiopaque materials include releasable and non-releasable agents which render the SNI visible in any known imaging technique such as X-ray radiographs, magnetic resonance imaging, computer assisted tomography and the like. The radiopaque material may be any conventional radiopaque material known in the art for allowing radiographic visualization of an implant, and may be, e.g., metal wire or flakes made from a biocompatible material, such as titanium, tantalum, stainless steel, or nitinol; or metallic salts (such as barium compounds).

Medicinal agents may be incorporated into the SNI at various points in the manufacturing process. For example, a suitable medicinal agent can be mixed with a hydrogel polymer solution before it is solvent cast. Alternatively, a suitable medicinal agent may be dissolved into a solvent cast solution and then diffuse into the hydrogel in accordance with normal kinetic principles. If the SNI is then dehydrated, the medicinal agent collects in the interstices of the hydrogel.

A radially compressed, dehydrated SNI according to the disclosure herein may be sterilized by any suitable conventional means, e.g., ethylene oxide, irradiation, etc. and packaged for distribution. A kit containing the sterilized SNI and a package insert describing the SNI, along with instructions is useful for medical practitioners. The radially compressed SNI may be implanted posteriorly or anteriorly, depending on the indication, into the disc space by making a small incision in the annulus which corresponds in size to the radial axis length (or less, e.g., one half radial axis length) of the SNI. In a preferred embodiment, an incision is made in the annulus which is less than the cross-sectional diameter of the dehydrated implant, e.g., approximately one-half the diameter of the dehydrated rod-shaped implant. A blunted or tapered end of the implant is inserted into the incision and the implant itself serves as a device for dilating the incision to substantially the cross-sectional dimensions of the SNI. In this manner, the length of the incision is minimized and efficiently sized directly to the implant cross-section. After passing through the annulus, the SNI is inserted into the disc space where it hydrates by absorption of fluid present in the disc space. See, FIGS. 4A, 4B and 5. In a preferred embodiment, the SNI is configured to expand (when it is not constrained by the end plates of the adjacent vertebrae) to a height which is greater than the disc space by about 5% to about 20% or greater. It is contemplated that, in one embodiment, a boomerang-like radially compressed SNI can be inserted which advantageously facilitates positioning of the SNI within the disc space by providing a SNI shape which partially conforms to the curved interior of the disc space. After insertion, the annulus may be sealed by any means known to those skilled in the art.

The following examples are included for purposes of illustrating certain aspects of preferred embodiments described herein. Accordingly, the examples are not to be construed as limiting any aspect of the subject matter disclosed herein.

EXAMPLE I

A hydrolyzate of poly(acrylonitrile) dissolved in an aqueous solvent was poured into a mold containing a cylindrical cavity 25 mm in diameter and 15 mm in height. Upon solidifying within the mold, the cast specimen maintains the mold cavity dimensions under certain swelling conditions. The $T_g$ of the specimen is well below room temperature. The specimen was placed into a sleeve of an interlocking poly(ethylene terepthalate) braid which is 150 mm in length and 5 mm in diameter. The ends of the braid are gripped tightly and tensioned by applying a constant 250 newton tensile load on the braid ends. The tensile load is converted to radial load on the specimen causing the specimen to elastically deform. Simultaneously, the specimen is exposed to a mild flow of less than about 75% relative humidity at about 70° F. causing the sample to slowly dehydrate. Twelve hours after exposure to air the $T_g$ of the specimen has been raised above room temperature. The specimen was removed from the tensioned braid and retained the deformed shape.

EXAMPLE II

Similar results specified in Example I may be achieved by raising the temperature of the xerogel above $T_g$, deforming the xerogel and lowering the temperature to less than $T_g$. A substantially dehydrated xerogel of poly(acrylonitrile) was cast from an aqueous solution into a 10 mm diameter sphere and solidified. After removing the cast it was dried to contain less than 2% water by weight. The xerogel was then heated to 105° C. and compressed under a load of 200 Newtons for 180 seconds. The resulting xerogel was rod-shaped, with a major axis of 10 mm and height of 1.5 mm. The xerogel hydrates to a spherical shape of 10 mm diameter at 90% water content.

It should be understood that the examples and embodiments of the invention provided herein are preferred embodiments. Various modifications may be made to these examples and embodiments without departing from the scope of the invention which is defined by the appended claims. For example, those skilled in the art may envision additional polymers and/or hydrogels which can be dehydrated and shaped according to the techniques described herein. Similarly, the shapes of the hydrated SNIs described herein are exemplary and any suitable hydrated SNI shape can be subjected to the techniques described herein to create an optimally shaped, substantially dehydrated SNI for minimally invasive insertion into the disc space. Those skilled in the art can envision additional radially collapsible members for exerting substantially uniform radial compression on the implant which are not set forth herein. In addition, process parameters such as temperature, humidity, pressure, time and concentration may be varied according to conventional techniques by those skilled in the art to optimize results.

What is claimed is:

1. A spinal nucleus implant comprising a hydrogel, the implant having at least first and second configurations, the first configuration occurring when the hydrogel is substantially dehydrated, the first configuration being a substantially rod-shaped monolithic solid body having a longitudinal axis defining the length of the rod-shaped solid body and a transverse axis defining the width of the rod-shaped solid body, the second configuration being a substantially ellipsoid solid body disc, wherein upon hydration of the substantially dehydrated hydrogel, the implant increases in volume by circumferential expansion along the transverse axis, from the first configuration to the second configuration.

2. A spinal nucleus implant according to claim 1 wherein the hydrogel is capable of anisotropic expansion.

3. A spinal nucleus implant according to claim 1 wherein the hydrogel is capable of isotropic expansion.

4. A spinal nucleus implant according to claim 1 wherein the substantially rod-shaped configuration is selected from the group consisting of can-shaped, cigar-shaped, suppository-shaped, torpedo-shaped and bullet-shaped.

5. A spinal nucleus implant according to claim 1 wherein both ends of the rod-shaped implant is blunted or tapered.

6. A spinal nucleus implant according to claim 1 wherein one end of the rod-shaped implant is blunted or tapered.

7. A spinal nucleus implant according to claim 1 wherein the rod-shaped configuration is substantially straight.

8. A spinal nucleus implant according to claim 1 wherein the rod-shaped configuration is curved into a boomerang-like shape.

9. A spinal nucleus implant according to claim 1 wherein the ellipsoid configuration is selected from the group consisting of elliptical, circular, kidney-shaped and heart shaped.

10. A spinal nucleus implant according to claim 1 wherein the implant comprises two or more component pieces which fit together and form the ellipsoid configuration.

11. A spinal nucleus implant according to claim 1 further comprising at least one reinforcing member which is interiorly disposed within the implant.

12. A spinal nucleus implant according to claim 1 further comprising at least one reinforcing member which is exteriorly disposed on the implant.

13. A spinal nucleus implant according to claim 1 wherein the implant contains at least two layers which are stacked axially, one on top of the other.

14. A spinal nucleus implant according to claim 1 wherein the length of the rod-shaped configuration is substantially equal to the major axis of the ellipsoid.

15. A spinal nucleus implant according to claim 1 wherein the hydrogel is a polyacrylonitrile copolymer.

16. A spinal nucleus implant according to claim 1 wherein the second configuration substantially fills a vertebral disc space.

17. A spinal nucleus implant according to claim 1 wherein the second configuration is adapted to expand to a height which is greater than the height of a vertebral disc space.

18. A spinal nucleus implant according to claim 1 wherein the first configuration is substantially rigid.

19. A spinal nucleus implant according to claim 1 wherein the first configuration is flexible.

20. A spinal nucleus implant according to claim 1 further comprising a medicinal agent.

21. A spinal nucleus implant according to claim 20 wherein the medicinal agent is an antimicrobial.

22. A spinal nucleus implant according to claim 20 wherein the medicinal agent is a radiopaque material.

23. A spinal nucleus implant according to claim 1 wherein the first configuration has less volume than the second configuration.

24. A spinal nucleus implant according to claim 1 wherein the cross-sectional area of the first configuration is less than about 50% of the second configuration.

25. A spinal nucleus implant according to claim 24 wherein the cross-sectional area of the first configuration is less than about 33% of the second configuration.

26. A spinal nucleus implant according to claim 25 wherein the cross-sectional area of the first configuration is less than about 25% of the second configuration.

27. A spinal nucleus implant according to claim 1 wherein the hydrogel is a closed cell structure.

28. A spinal nucleus implant according to claim 27 wherein the hydrogel comprises a continuous phase selected from the group consisting of a hydrophilic polymer and a hydrophobic polymer, and a dispersed phase of a hydrophilic polymer.

29. A spinal nucleus implant comprising a hydrogel, the implant having first and second configurations, the first configuration occurring when the hydrogel is substantially dehydrated, the first configuration being a substantially rod shaped compressed monolithic solid body having a longitudinal axis defining the length of the rod-shaped compressed solid body and a transverse axis defining the width of the rod-shaped solid body, the second configuration being a substantially ellipsoid disc, wherein upon hydration of the substantially dehydrated hydrogel, the implant increases in volume by circumferential expansion along the transverse axis, from the first configuration to the second configuration.

30. A spinal nucleus implant according to claim 29 wherein the hydrogel is capable of anisotropic expansion.

31. A spinal nucleus implant according to claim 29 wherein the hydrogel is capable of isotropic expansion.

32. A spinal nucleus implant according to claim 29 wherein the substantially rod-shaped configuration is selected from the group consisting of can-shaped, cigar-shaped, suppository-shaped, torpedo-shaped and bullet-shaped.

33. A spinal nucleus implant according to claim 29 wherein the rod-shaped configuration is substantially straight.

34. A spinal nucleus implant according to claim 29 wherein the rod-shaped configuration is curved into a boomerang-like shape.

35. A spinal nucleus implant according to claim 29 wherein the ellipsoid disc configuration is selected from the group consisting of elliptical, circular, kidney-shaped and heart shaped.

36. A spinal nucleus implant according to claim 29 wherein the implant comprises two or more component pieces which fit together and form the ellipsoid disc configuration.

37. A spinal nucleus implant according to claim 29 further comprising at least one reinforcing member which is interiorly disposed within the implant.

38. A spinal nucleus implant according to claim 29 further comprising at least one reinforcing member which is exteriorly disposed on the implant.

39. A spinal nucleus implant according to claim 29 wherein the implant contains at least two layers which are stacked axially, one on top of the other.

40. A spinal nucleus implant according to claim 29 wherein the length of the rod-shaped configuration is substantially equal to the major axis of the ellipsoid.

41. A spinal nucleus implant according to claim 29 wherein the hydrogel is a polyacrylonitrile copolymer.

42. A spinal nucleus implant according to claim 29 wherein the second configuration is adapted to substantially fill a vertebral disc space.

43. A spinal nucleus implant according to claim 29 wherein the second configuration is adapted to expand to a height which is greater than the height of a vertebral disc space.

44. A spinal nucleus implant according to claim 29 wherein the first configuration is substantially rigid.

45. A spinal nucleus implant according to claim 29 wherein the first configuration is flexible.

46. A spinal nucleus implant according to claim 29 further comprising a medicinal agent.

47. A spinal nucleus implant according to claim 29 wherein the medicinal agent is a radiopaque material.

48. A spinal nucleus implant comprising a hydrogel, the hydrogel having at least first and second phases, the implant having at least first and second configurations, the first configuration occurring when the hydrogel is substantially dehydrated to amount of about 2% to about 30% water by weight, the first configuration being a substantially rod-shaped monolithic solid body having a longitudinal axis defining the length of the rod-shaped solid body and a transverse axis defining the width of the rod-shaped solid body, the second configuration being a substantially ellipsoid solid body disc, wherein upon hydration of the first phase with water to an amount of about 60% to about 90% by weight of the substantially dehydrated hydrogel, the implant increases in volume by circumferential expansion along the transverse axis, from the first configuration to the second configuration.

49. A spinal nucleus implant according to claim 48 wherein the substantially rod-shaped configuration is selected from the group consisting of can-shaped, cigar-shaped, suppository-shaped, torpedo-shaped and bullet-shaped.

50. A spinal nucleus implant according to claim 48 wherein the ellipsoid configuration is selected from the group consisting of elliptical, circular, kidney-shaped and heart shaped.

51. A spinal nucleus implant according to claim 48 further comprising at least one reinforcing member which is interiorly disposed in the implant or exteriorly disposed on the implant.

52. A spinal nucleus implant according to claim 48 wherein the implant contains at least two layers which are stacked axially, one on top of the other.

53. A spinal nucleus implant according to claim 48 wherein the hydrogel is a polyacrylonitrile copolymer.

54. A spinal nucleus implant according to claim 48 wherein the second configuration is adapted to expand to a height which is greater than the height of a vertebral disc space.

55. A spinal nucleus implant according to claim 48 further comprising a medicinal agent.

\* \* \* \* \*